(12) United States Patent
Scattergood et al.

(10) Patent No.: US 9,611,431 B2
(45) Date of Patent: *Apr. 4, 2017

(54) METHOD OF REDUCING CORROSION AND CORROSION BYPRODUCT DEPOSITION IN A CRUDE UNIT

(71) Applicant: Nalco Company, Naperville, IL (US)

(72) Inventors: Glenn L. Scattergood, Sugar Land, TX (US); Sam Ferguson, Sugar Land, TX (US)

(73) Assignee: NALCO COMPANY, Naperville, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/874,675

(22) Filed: Oct. 5, 2015

(65) Prior Publication Data

US 2016/0024395 A1    Jan. 28, 2016

Related U.S. Application Data

(63) Continuation of application No. 12/263,904, filed on Nov. 3, 2008, now Pat. No. 9,150,793.

(51) Int. Cl.
*C10G 7/10*      (2006.01)
*C10G 7/12*      (2006.01)
*C10G 75/02*     (2006.01)
*C10G 31/08*     (2006.01)

(52) U.S. Cl.
CPC ............... *C10G 7/12* (2013.01); *C10G 7/10* (2013.01); *C10G 31/08* (2013.01); *C10G 75/02* (2013.01); *C10G 2300/4075* (2013.01)

(58) Field of Classification Search
None
See application file for complete search history.

(56) References Cited

U.S. PATENT DOCUMENTS

| | | |
|---|---|---|
| 3,740,722 A | 6/1973 | Greenberg et al. |
| 3,779,905 A | 12/1973 | Stedman |
| 3,819,328 A | 6/1974 | Go |
| 4,238,349 A | 12/1980 | Larsen et al. |
| 4,335,072 A | 6/1982 | Barnett et al. |
| 4,425,267 A | 1/1984 | Skripchik et al. |
| 5,066,199 A | 11/1991 | Reese et al. |
| 5,094,958 A | 3/1992 | Klainer et al. |
| 5,195,879 A | 3/1993 | Reese et al. |
| 5,256,276 A | 10/1993 | Weaver |
| 5,302,253 A | 4/1994 | Lessard et al. |
| 5,324,665 A | 6/1994 | Lessard |
| 5,326,482 A | 7/1994 | Lessard et al. |
| 5,425,267 A | 6/1995 | Herrmann et al. |
| 5,503,006 A | 4/1996 | Babaian-Kibala et al. |
| 5,965,785 A | 10/1999 | Braden et al. |
| 7,744,276 B2 | 6/2010 | Webb |
| 8,712,335 B2 | 4/2014 | Mathur et al. |
| 9,150,793 B2 * | 10/2015 | Scattergood et al. .... C10G 7/10 |
| 2007/0025412 A1 | 2/2007 | Webb |
| 2007/0077176 A1 | 4/2007 | Lambert et al. |
| 2007/0152813 A1 | 7/2007 | Mathur et al. |
| 2009/0149981 A1 | 6/2009 | Evans et al. |
| 2010/0108566 A1 | 5/2010 | Scattergood et al. |
| 2011/0282614 A1 | 11/2011 | Kiyono |
| 2012/0053861 A1 | 3/2012 | Kremer et al. |
| 2012/0092646 A1 | 4/2012 | Stolberg-Rohr et al. |
| 2014/0053837 A1 | 2/2014 | Klein |

FOREIGN PATENT DOCUMENTS

| | | |
|---|---|---|
| EP | 1298185 A1 | 4/2003 |
| GB | 1198734 A | 7/1970 |
| WO | WO 03/006581 A2 | 1/2003 |
| WO | WO 2004/044266 A1 | 5/2004 |
| WO | WO 2008/005058 A1 | 1/2008 |

OTHER PUBLICATIONS

Conant, "Wireless Sensor Networks: Driving the New Industrial Revolution," *Industrial Embedded Systems*, Apr. 2006.
Little et al., "How to Control . . . Crude Unit Overhead Corrosion," *Hydrocarbon Processing*, 56(5), 1977, pp. 205-207.
Szyprowski et al., "Anticorrosion Technology Demonstrated at Polish Refinery," *Oil and Gas Journal*, 85(18), 1987, pp. 33-37.

* cited by examiner

*Primary Examiner* — Randy Boyer
(74) *Attorney, Agent, or Firm* — Leydig, Voit & Mayer, Ltd.

(57) ABSTRACT

A method of optimizing system parameters in a crude unit to reduce corrosion and corrosion byproduct deposition in the crude unit is disclosed and claimed. The method includes measuring or predicting properties associated with the system parameters and using an automated controller to analyze the properties to cause adjustments in the chemical program to optimize the system parameters. Adjusting the system parameters effectively controls corrosion in the crude unit by reducing the corrosiveness of a fluid in the process stream and/or by protecting the system from a potentially corrosive substance. System parameter sensing probes are arranged at one or more locations in the process stream to allow accurate monitoring of the system parameters in the crude unit.

21 Claims, 7 Drawing Sheets

METHOD OF REDUCING CORROSION AND CORROSION BYPRODUCT DEPOSITION IN A CRUDE UNIT

This application is a continuation of U.S. patent application Ser. No. 12/263,904, which was filed Nov. 3, 2008, the disclosure of which is incorporated herein by reference in its entirety.

TECHNICAL FIELD

This invention relates generally to methods of reducing corrosion in a crude unit. More specifically, the invention relates to methods of optimizing system parameters in a process stream of a crude unit to reduce corrosion in the crude unit. The invention has particular relevance to sampling dew point water and accumulator boot water to measure system parameters and respond to such measurements to reduce corrosion and/or corrosion byproduct deposition in the crude unit.

BACKGROUND

In a crude oil refinery, generally the oil is pumped from a storage tank to a crude unit for processing. The crude unit cleans the oil through water washing in a desalter and then splits the oil into fractions in an atmospheric distillation tower. These fractions are pumped to various processing units downstream of the crude unit (e.g., coker, catalytic cracker, hydrotreater etc.). Though corrosion and corrosion byproduct deposition (the latter sometimes referred to herein as fouling) occur in many areas of a crude unit, the most severe corrosion and fouling typically take place in the overhead condensing system of the atmospheric distillation tower.

Refinery crude unit processing has becoming increasingly difficult in recent years and is predicted to become even more challenging and complex for several reasons. For example, significant increases in crude oil prices have caused refiners to aggressively pursue "opportunity" or "challenging" crudes that are obtainable at discounted prices. The lower price is linked to a crude property such as high acid or high solids content that makes it less desirable than the light, sweet benchmark crudes.

Refiners switch crude slates more frequently than in the past due to minimum on-hand crude oil inventory combined with increased crude oil variety. A crude slate switch typically upsets the steady state condition of a crude unit for up to several hours. Generally, about eighty percent of the corrosion and fouling occurs during these switches or disruptions, which normally last about twenty percent of the time. If fouling and corrosion issues are severe enough, the refiner will discontinue processing the crude oil or blend of crudes causing the problem. However, these challenging crudes are available to the refiner at a discount thus making them more profitable. Discontinuing such problematic crudes is accordingly not a very popular option.

In efforts to reduce corrosion, a crude unit may be serviced two or three dines per week, or in sonic cases daily. Daily service at best provides a snap shot view of a dynamic crude unit system. Crude type and/or raw crude storage tanks are switched several times per week, sometimes daily. The contents of each tank are different from the others, so each switch causes a change of feed quality to the crude unit, many times upsetting the steady state status and causing disruptions in the system. Preheating, desalting, and distilling operations shift with the new crude, sending products and/or effluent water sources off specification. Many adjustments over several hours (in some cases days) normally take place to return the crude unit to steady state operation.

The most common current industry practice to control such disruptions and optimize crude unit operation is to provide enough manpower and man-hours. For instance, each crude unit may have an operating crew from three to ten people, depending on size and complexity of the unit. This crew may spend their day gathering various samples for wet chemistry lab testing, and measuring and making adjustments for temperature and flow to keep the unit running within specification. Such practice is typically geared towards keeping the unit operating properly with respect to fractionation quality cut points and end points, with minimal attention being paid to a specialty chemical corrosion control program. If a disruption is severe, changes may be made to the process chemicals and/or changes in levels, flows, or temperatures may be recommended around the crude unit to keep the dynamic system in as optimum a condition as possible.

Attempts to compensate for periodic or sometimes prolonged lack of human involvement include installing online pH meters on atmospheric distillation towers overhead accumulator water boots; however, due to a high rate of fouling of the pH sensor only a small percentage of these meters operate correctly for any length of time. Online instrumentation, such as pH meters, requires routine maintenance and calibration. Moreover, online pH merely tracks the pH and sends an alarm to the operator when the pH is outside the control limits. Often, poorly calibrated and/or fouled pH meters cause frequent alarms. This frequency tends to minimize the effectiveness of the alarm system.

Due to the lack of industry success with online pH metering and other monitoring efforts refiners have not pursued more exotic and effective online instrumentation for process chemical programs. There thus exists an ongoing need for more sophisticated and effective online and/or automatic methods for monitoring parameters and reducing corrosion in crude units.

SUMMARY

This invention accordingly provides methods to generate reliable crude unit data in a feedback, feed-forward, or predictive loop(s) to make real-time adjustments to process stream treatments thus reducing corrosion and corrosion byproduct deposition (sometimes referred to herein as fouling). In a preferred aspect, the invention is implemented to provide continuous or intermittent feedback, feed-forward, or predictive information to process chemical injection pumps to make real-time adjustments. The invention incorporates programming logic to convert analyzer signals to pump adjustment logic and, in a preferred embodiment, controls one or each of a plurality of chemical injections with a unique basis. Examples include neutralizer injection based on pH, chloride, or acid content; caustic agent injection based on pH, chloride, or acid content; and filming inhibitor injection based on iron concentration or corrosion rate.

It is also envisioned that the invention will manage the readings from existing electrical resistance corrosion probes, linear polarization probes, and/or other techniques for measuring metal loss. These readings will be programmed through a Programming Logic Controller (PLC) to possibly override or modify the other chemical inputs and change pump rates. Moreover, because the crude unit atmospheric distillation tower overhead heat exchanger system suffers frequent and costly issues with corrosion, the invention focuses on that part of the crude unit. However, the invention has utility on many other units in the refinery.

In an aspect, the invention includes a method of optimizing a system parameter in a process stream of a crude unit to reduce corrosion in the crude unit. A property associated with the system parameter is measured and/or predicted at or more points in the crude unit and is converted into an input electrical signal capable of being transmitted to a controller. In turn, the controller is operable to receive the transmitted input electrical signal, convert the received electrical signal into an input numerical value, analyze the input numerical value, generate an output numerical value, convert the output numerical value into an output electrical signal, and transmit the output electrical signal. An optimum corrosion-reducing range for the input numerical value is determined and if the input numerical value is outside of the optimum range, the transmitted output electrical signal causes a change in an influx of a composition into the process stream. The composition is capable of adjusting the property associated with the system parameter in a manner to bring the input numerical value within the optimum range. In an embodiment, an influx of one or more different compositions into the process stream are collectively and/or individually capable of adjusting the property(ies) associated with the system parameter(s). The method is optionally repeated for a plurality of different system parameters, where each different system parameter has a unique associated property.

In another aspect, the invention includes a system for optimizing a system parameter in a process stream of a crude unit to reduce corrosion in the crude unit. The system comprises a sensing device operable to sense and/or predict a property associated with the system parameter and convert the property into an input electrical signal capable of being transmitted. A transmitter transmits the input electrical signal to a controller. The controller is operable to receive the transmitted input electrical signal, convert the received input electrical signal into an input numerical value, analyze the input numerical value to determine if the input numerical value is in an optimum range, generate an output numerical value, convert the output numerical value into an output electrical signal, and transmit the output electrical signal. A receiver receives the output electrical signal and is operable to cause a change in an influx rate of a composition into the process stream if the output numerical value is not within the optimum range, wherein the composition is capable of adjusting the property associated with the system parameter.

In an embodiment, one or more of the described controller functions may be imparted to one or more data capturing devices.

It is an advantage of the invention to provide continuous control of one or more key process corrosion control chemicals, an improvement over the current practice of manual, highly variable frequency optimization.

Another advantage of the invention is to provide a method to achieve optimum efficiency through reduced corrosion and fouling, minimizing the amount of product that does not meet specification, and reducing the amount of slop oil processing.

It is another advantage of the invention to provide an automated process to efficiently minimize disruptions and the resulting corrosion and fouling caused by a switch between various types of crude slates, including challenging crude, and minimize corrosion, disruptions, and downtime during such switching.

It is a further advantage of the invention to provide continuous data to measure the magnitude of a disruption and to more precisely identify the root cause of a disruption, including determining the concentration of corrosion byproduct(s) formed in the system due to a spike in corrosion during a disruption.

An additional advantage of the invention is to provide a method of optimizing system efficiency when crude slates are changed by quickly stabilizing system operating parameters.

It is yet another advantage of the invention to provide data leading to a level of corrosion control that will help prevent expensive metallurgy upgrades in crude refining systems in order to process acidic crudes.

Additional features and advantages are described herein, and will be apparent from, the following Detailed Description, Examples, and Figures.

DETAILED DESCRIPTION

As one of the main components of a crude unit process, corrosion control plays a vital role in maintaining system integrity. This invention provides a way to optimize the corrosion control component of the crude unit through optimizing one or more system parameters in a process stream of the crude unit. This optimization includes measuring properties associated with those parameters in the process stream.

The corrosion control program of the invention is designed to reduce corrosion of refinery processing equipment and subsequent fouling due to deposition of corrosion byproducts. A typical corrosion control program includes components such as a neutralizing amine, a filming inhibitor, a caustic solution, etc. Such corrosion control chemicals are traditionally injected into the system based upon measurements derived from grab samples and analyzed in the lab or some flow indication on the unit. This invention provides an automated method of adjusting chemical injection into the system.

In a preferred embodiment, the method of the invention includes a controller operable to receive and process information and provide instructions to various components (e.g., chemical injection pumps). The term "controller" refers to a manual operator or an electronic device having components such as a processor, memory device, digital storage medium, cathode ray tube, liquid crystal display, plasma display, touch screen, or other monitor, and/or other components. The controller is preferably operable for integration with one or more application-specific integrated circuits, programs, computer-executable instructions or algorithms, one or more hard-wired devices, wireless devices, and/or one or more mechanical devices. Moreover, the controller is operable to integrate the feedback, feed-forward, or predictive loop(s) of the invention. Some or all of the controller system functions may be at a central location, such as a network server, for communication over a local area network, wide area network, wireless network, internet connection, microwave link, infrared link, and the like. In addition, other components such as a signal conditioner or system monitor may be included to facilitate signal transmission and signal-processing algorithms.

Preferably, the controller includes hierarchy logic to prioritize any measured or predicted properties associated with system parameters. For example, the controller may be programmed to prioritize system pH over chloride ion concentration or vice versa. It should be appreciated that the object of such hierarchy logic is to allow improved control over the system parameters and to avoid circular control loops.

In one embodiment, the method includes an automated controller. In another embodiment, the controller is manual or semi-manual. For example, where the crude refining process includes one or more datasets received from a various sensors in the system, the controller may either automatically determine which data points/datasets to further process or an operator may partially or fully make such a determination. A dataset from a crude unit, for instance, may include variables or system parameters such as oxidation-reduction potential, pH, levels of certain chemicals or ions (e.g., determined empirically, automatically, fluorescently, electrochemically, colorimetrically, measured directly, calculated), temperature, pressure, process stream flow rate, dissolved or suspended solids, etc. Such system parameters are typically measured with any type of suitable data capturing equipment, such as pH sensors, ion analyzers, temperature sensors, thermocouples, pressure sensors, corrosion probes, and/or any other suitable device or method. Data capturing equipment is preferably in communication with the controller and, according to alternative embodiments, may have advanced functions (including any part of the control algorithms described herein) imparted by the controller.

Data transmission of measured parameters or signals to chemical pumps, alarms, or other system components is accomplished using any suitable device, such as a wired or wireless network, cable, digital subscriber line, internet, etc. Any suitable interface standard(s), such as an ethernet interface, wireless interface (e.g., IEEE 802.11a/b/g/x, 802.16, Bluetooth, optical, infrared, radiofrequency, etc.), universal serial bus, telephone network, the like, and combinations of such interfaces/connections may be used. As used herein, the term "network" encompasses all of these data transmission methods. Any of the described devices (e.g., plant archiving system, data analysis station, data capture device, process station, etc.) may be connected to one another using the above-described or other suitable interface or connection.

In an embodiment, system parameter information is received from the system and archived. In another embodiment, system parameter information is processed according to a timetable or schedule. In a further embodiment, system parameter information is immediately processed in real-time/substantially real-time. Such real-time reception may include, for example, "streaming data" over a computer network.

Figure 1:
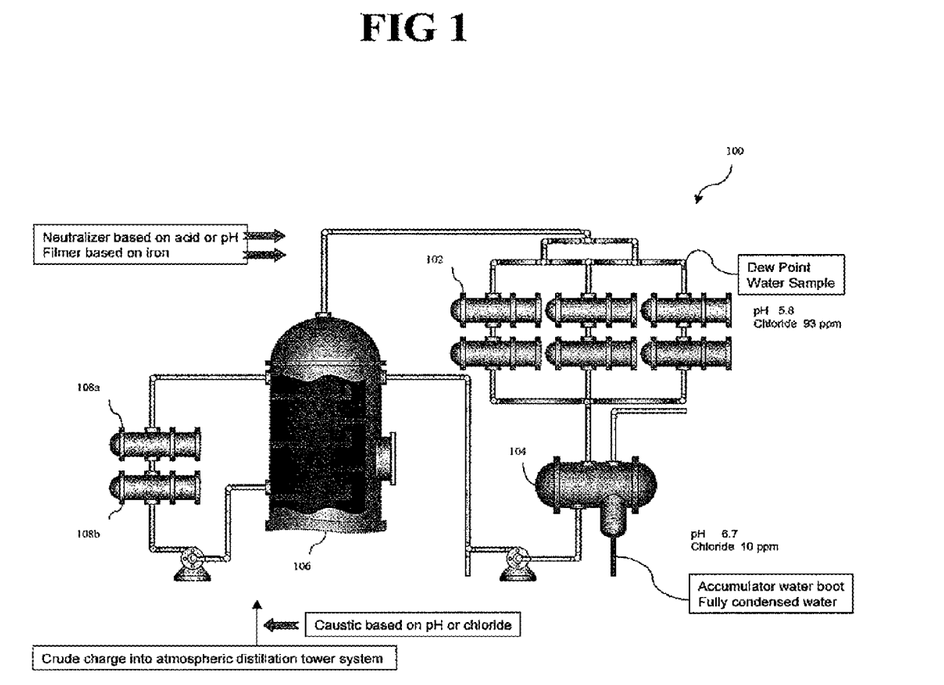
FIG. 1 is a diagrammatic view of an embodiment of the invention showing various crude unit components and exemplary points at which system parameters are measured.

Referring now to the Figures, FIG. 1 depicts a diagram of a preferred embodiment of the invention. It should be appreciated that the particular configuration of the crude unit is not critical to the invention and FIG. 1 illustrates one possible configuration. FIG. 1 shows a typical atmospheric distillation tower system 100 of a crude unit that includes overhead heat exchanger bank 102, accumulator 104, distillation tower 106, and pumparound heat exchangers 108a and 108b. In this embodiment, a dew point water sample is obtained at the indicated point and a sample of accumulator boot water is obtained at the indicated points on FIG. 1. These samples are measured and analyzed for the system parameters of pH, chloride ion concentration, and iron ion concentration.

FIG. 1 shows values of 5.8 for pH and 93 ppm for chloride ion concentration at the dew point water sample point and values of 6.7 and 10, respectively, at the accumulator boot sample point. The measurement differences at these two sample points require a corresponding algorithm to adjust chemical injection. The preferred location in the crude unit for determining pH and chloride ion concentration is a dew point water sample, usually derived from the overhead heat exchangers of the distillation tower. Another advantage of determining pH from the dew point water is that the pH probe encounters lower levels of contaminants and fewer solid particles and oil droplets resulting in less frequent fouling. The term "dew point" refers to the point of initial condensation of steam to water or the temperature at which a phase of liquid water separates from the water vapors and liquid hydrocarbons and begins to form liquid water as the vapors cool. Though possible to use the accumulator water boot to measure pH and chloride ion level, a level of accuracy is usually sacrificed because data is diluted or masked by the full volume of steam and weak acids and bases that have condensed downstream of the water dew point.

In a preferred embodiment, dew point water is analyzed for pH and chloride. It is advantageous to analyze dew point water rather than overhead accumulator water for pH and chloride because the dew point water is typically cleaner and provides a faster response with more accurate measurement of these system parameters. Testing usually reveals a dramatic difference between water samples from these two locations. On many units, the dew point chloride concentration may be several hundred ppm, while a similar sample taken from overhead accumulator water may, at the same time, be from 10 to 50 ppm. For example, dew point water may have a pH of 5.8 and a chloride ion concentration of 93 ppm; whereas, the accumulator boot water of the same unit may have values of 6.7 and 10, respectively.

Likewise, it is possible to measure iron (or other metals, such as copper, molybdenum, nickel, zinc) ion concentration from the dew point water. The preferred location for determining iron or other metal ion concentration is at the accumulator water boot because these ions indicate corrosion has taken place and metal has been removed from an internal component in the system upstream of the sample point.

It should be appreciated that any suitable method may be used for obtaining the dew point water sample. For example, devices for obtaining the dew point water sample are disclosed in U.S. Pat. Nos. 4,335,072, titled "Overhead Corrosion Simulator" and 5,425,267, titled "Corrosion Simulator and Method for Simulating Corrosion Activity of a Process Stream," each of which is incorporated herein by reference in its entirety.

In alternative embodiments, different fluid or system parameters or other constituents present in the system could be measured and/or analyzed. Representative measured parameters or constituents include pH; chloride ion; other strong and weak acids, such as sulfuric, sulfurous, thiosulfurous, carbon dioxide, hydrogen sulfide; organic acids; ammonia; various amines; and liquid or solid deposits. Various methods of measuring such parameters are contemplated and the invention is not limited to one particular method. Representative methods include, but are not limited to those disclosed in U.S. Pat. Nos. 5,326,482, titled "On-Line Acid Monitor and Neutralizer Feed Control of the Overhead Water in Oil Refineries"; 5,324,665, titled "On-Line Method for Monitoring Chloride Levels in a Fluid Stream"; 5,302,253, titled "On-Line Acid Monitor and Neutralizer Feed Control of the Overhead Water in Oil Refineries," each of which is incorporated herein by reference in its entirety.

In response to the measured system parameters, FIG. 1 shows exemplary introduction points for neutralizers, filming inhibitors (sometimes referred to herein as "filmers"), and caustic agents. These points are labeled "Neutralizer based on acid or pH," "Filmer based on iron," and "Caustic based on chloride." It should be appreciated that such chemicals may be added at any suitable location in the system, but are preferably added at the indicated point on FIG. 1. In this embodiment, neutralizer and filming inhibitor is added upstream of overhead heat exchanger bank 102 and caustic agent is added into the crude oil charge of atmospheric distillation tower system 100. According to a preferred embodiment, introduction of such chemicals into the system are adjusted continuously. In other embodiments, chemical introduction is adjusted intermittently or in relation to a schedule as determined for each individual system.

Neutralizer(s), caustic agent(s), and filming inhibitor(s) may be introduced to the system using any suitable type of chemical feed pump. Most commonly, positive displacement injection pumps are used powered either electrically or pneumatically. Continuous flow injection pumps are sometimes used to ensure specialty chemicals are adequately and accurately injected into the rapidly moving process stream. Though any suitable pump or delivery system may be used, exemplary pumps and pumping methods include those disclosed in U.S. Pat. Nos. 5,066,199, titled "Method for Injecting Treatment Chemicals Using a Constant Flow Positive Displacement Pumping Apparatus" and 5,195,879, titled "Improved Method for Injecting Treatment Chemicals Using a Constant Flow Positive Displacement Pumping Apparatus," each incorporated herein by reference in its entirety.

Representative neutralizers include but are not limited to 3-methoxypropylamine (MOPA) (CAS #5332-73-0), monoethanolamine (MEA) (CAS #141-43-5), N,N-dimethylaminoethanol (DMEA) (CAS #108-01-0), and methoxyisopropylamine (MIOPA) (CAS #37143-54-7).

As a caustic agent, a dilute solution of sodium hydroxide is typically prepared in a 5 to 10% concentration (7.5 to 14° Baume) for ease of handling and to enhance distribution once injected into the crude oil, or desalter wash water, for example. Concentration may be adjusted according to ambient conditions, such as for freeze point in cold climates.

Filming inhibitors or filmers used in conjunction with this invention in a crude unit corrosion control program are typically oil soluble blends of amides and imidazolines. These compounds offer good corrosion control with minimal effects on the ability of the hydrocarbons in the system to carry water.

Figure 2:
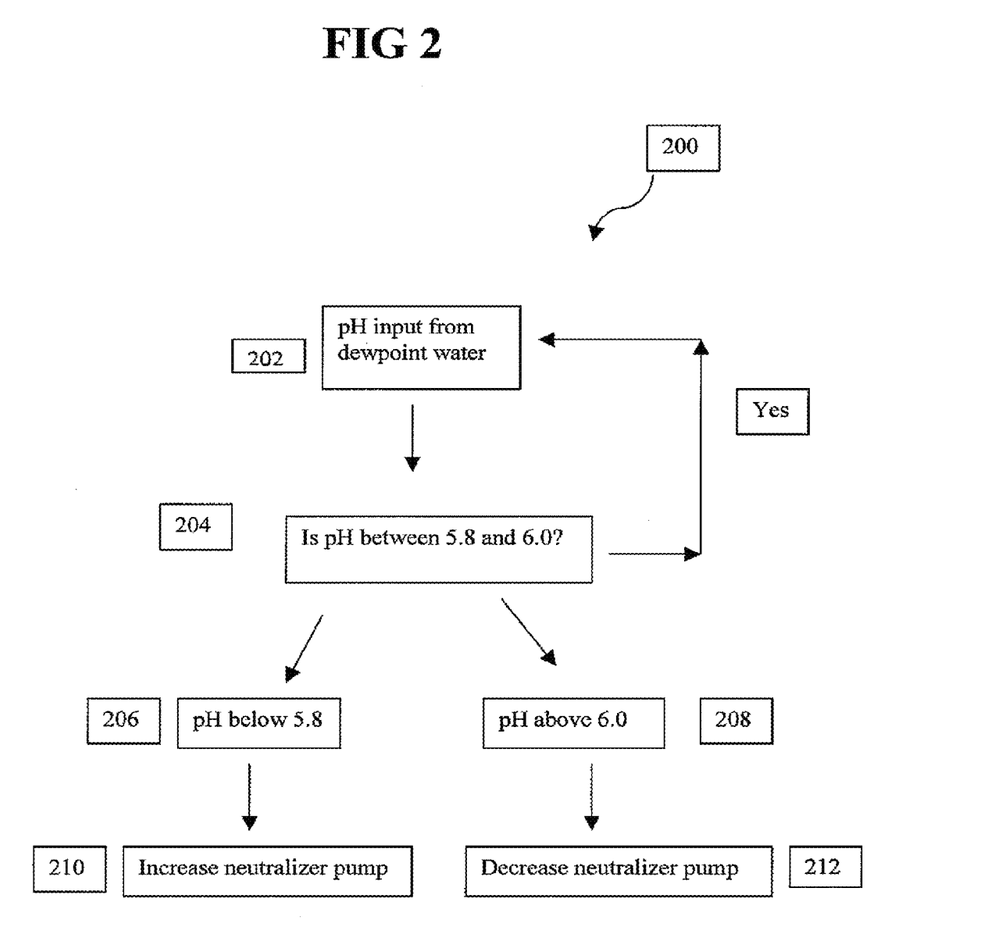
FIG. 2 shows a flowchart of a preferred embodiment of controlling the introduction of neutralizer(s) into the system based upon measured pH.

FIG. 2 shows a flowchart of a preferred embodiment of controlling the introduction of neutralizer(s) into the system based upon measured pH, labeled method 200. Box 202 represents the measuring device or analyzer that provides information related to the pH of the dew point (or accumulator) water. The analyzer (e.g., controller or operator) determines whether the pH is within an optimum range (5.8 to 6.0 in this example) as shown in box 204. If the pH is within the predetermined optimum range, the logic follows the "Yes" path and continues measuring and analyzing. If the pH is not within this range, the method includes determining whether the pH is below 5.8, as represented by box 206, or above 6.0, as represented by box 208. If the pH is below 5.8, the method includes increasing the neutralizer pump by, for example, 5% or 10%, as shown by box 210. If the pH is above 6.0, the method includes decreasing the neutralizer pump by, for example, 5% or 10%, as shown by box 212.

It should be appreciated that a suitable pH control or optimal range should be determined for each individual system. The optimum range for one system may vary considerably from that for another system. It is within the concept of the invention to cover any possible optimum pH range.

In different embodiments, changes in the neutralizer pump are limited in frequency. Preferably, adjustment limits are set at a maximum of 1 per 15 min and sequential adjustments in the same direction should not exceed 8. For example, after 8 total adjustments or a change of 50% or 100%, the pump could be suspended for an amount of time (e.g., 2 or 4 hours) and alarm could be triggered. If such a situation is encountered, it is advantageous to trigger an alarm to alert an operator. Other limits, such as maximum pump output may also be implemented. It should be appreciated that it is within the scope of the invention to cause any number of adjustments in any direction without limitation. Such limits are applied as determined by the operator.

Figure 3:
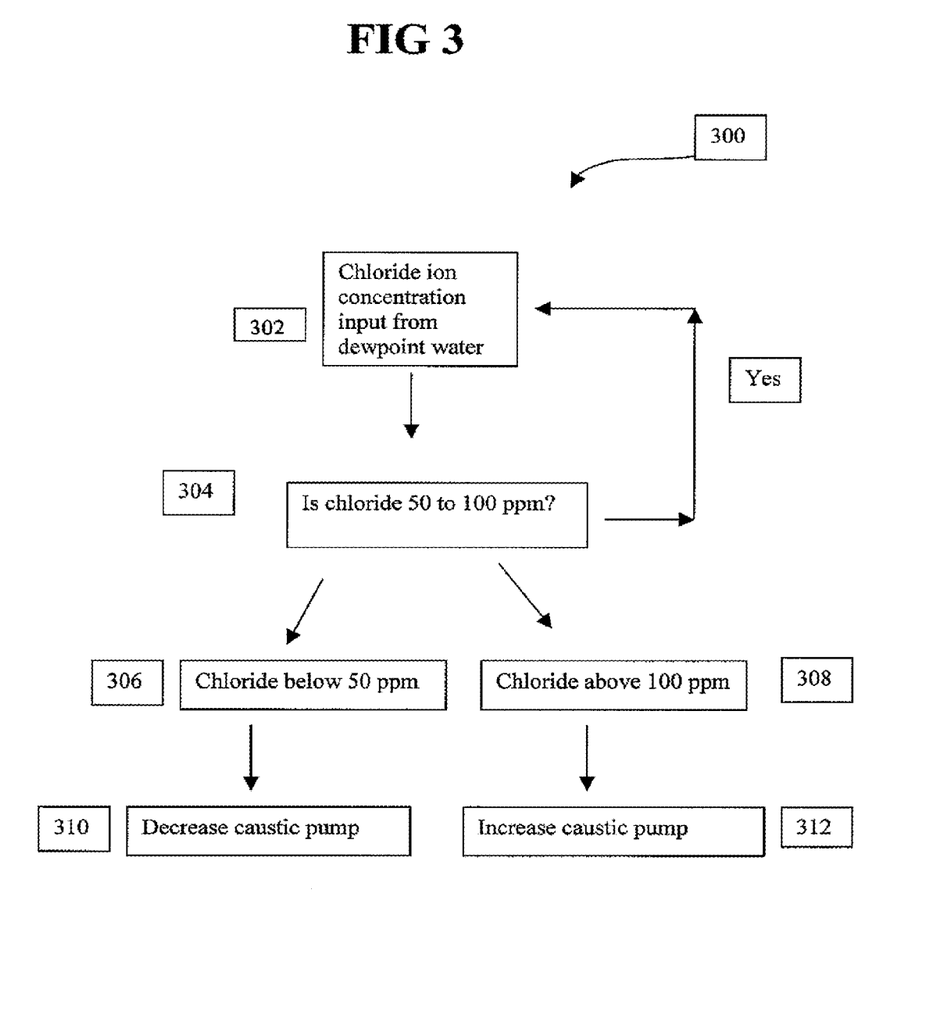
FIG. 3 illustrates an embodiment of the invention for controlling the introduction of caustic agent(s) into the system driven by the chloride ion concentration signal.

FIG. 3 illustrates an embodiment of the invention as method 300 for controlling the introduction of caustic agent(s) into the system driven by the chloride ion concentration signal. Box 302 represents the measuring device or analyzer that provides information related to the chloride ion concentration of the dew point water. The analyzer (e.g., controller or operator) determines whether the chloride ion concentration is within an optimum range (50 to 100 ppm in this example) as shown in box 304. If the chloride ion concentration is within the predetermined optimum range, the logic follows the "Yes" path and continues measuring and analyzing. If the chloride ion concentration is not within this range, the method includes determining whether the chloride ion concentration is below 50 ppm, as represented by box 306, or above 100 ppm, as represented by box 308. If the chloride ion concentration is below 50 ppm, the method includes decreasing the caustic pump by, for example, 20%, as shown by box 310. If the chloride ion concentration is above 100 ppm, the method includes increasing the caustic pump by, for example, 20%, as shown by box 312.

It should be appreciated that a suitable or optimal chloride ion concentration range should be determined for each individual system. The optimum range for one system may vary considerably from that for another system. It is within the concept of the invention to cover any possible optimum chloride ion concentration range.

In different embodiments, changes in the caustic pump are limited in frequency. Preferably, adjustment limits are set at a maximum of 1 per 30 min and sequential adjustments in the same direction should not exceed 4. For example, after 4 total adjustments or a change of 50% or 100%, the pump could be suspended for an amount of time (e.g., 2 or 4 hours) and alarm could be triggered. If such a situation is encountered, it is advantageous to trigger an alarm to alert an operator. Other limits, such as maximum pump output or maximum sodium contribution to the system may also be implemented. It should be appreciated that it is within the scope of the invention to cause any number of adjustments in any direction without limitation. Such limits are applied as determined by the operator.

Figure 4:
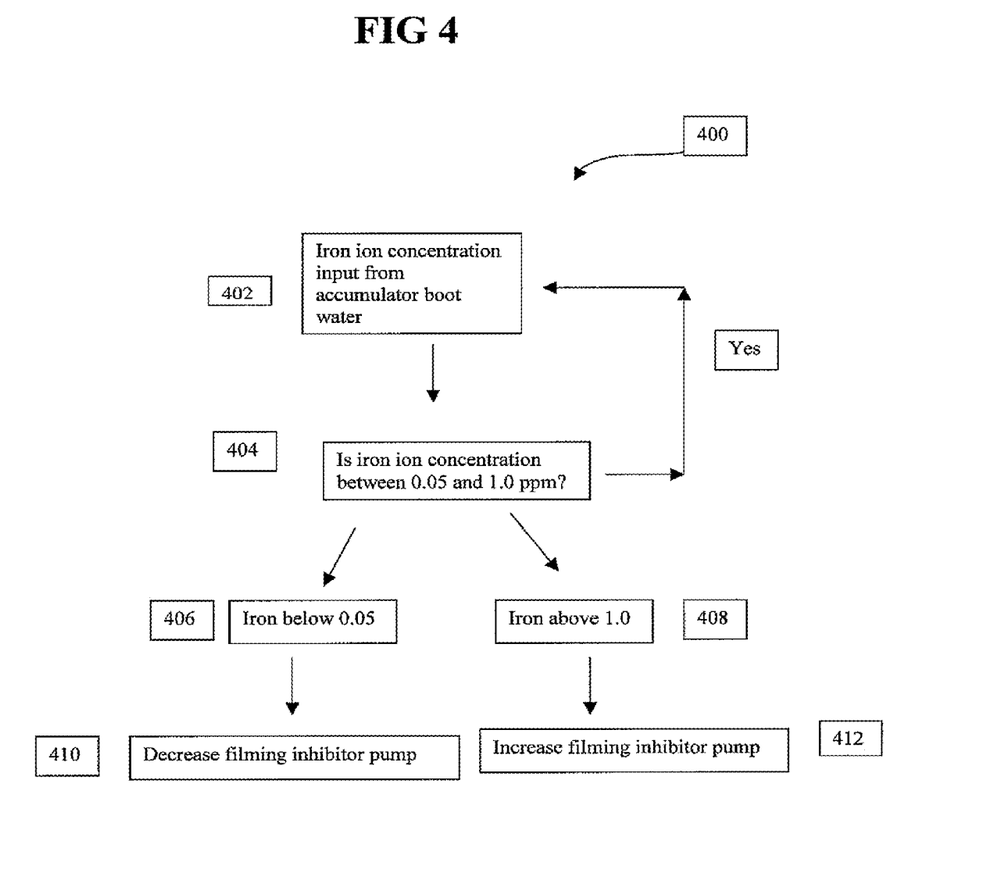
FIG. 4 illustrates an embodiment of the invention for controlling the introduction of filming inhibitors into the system driven by the iron ion concentration signal.

FIG. 4 illustrates an embodiment of the invention as method 400 for controlling the introduction of filming inhibitors into the system driven by the iron ion concentration signal. Other metallurgy, such as monel, titanium, brass, etc. may be used in some systems. In these cases, rather than an iron ion concentration signal, the appropriate metal ion (e.g., copper, nickel, zinc, etc.) concentration signal would be detected and analyzed. Box 402 represents the measuring device or analyzer that provides information related to the iron ion concentration of the accumulator boot water. The analyzer (e.g., controller or operator) determines whether the iron ion concentration is within an optimum range (0.05 to 1.0 ppm in this example) as shown in box 404. If the iron ion concentration is within the predetermined optimum range, the logic follows the "Yes" path and continues measuring and analyzing. If the iron ion concentration is not within this range, the method includes determining whether the iron ion concentration is below 0.05 ppm, as represented by box 406, or above 1.0 ppm, as represented by box 408. If the iron ion concentration is below 0.05 ppm, the method includes decreasing the filming inhibitor (i.e., filmer) pump by, for example, 5%, as shown by box 410. If the iron ion concentration is above 1.0 ppm, the method includes increasing the filmer pump by, for example, 5%, as shown by box 412.

Metal ions commonly exist in two or more oxidation states. For example, iron exists in $Fe^{2+}$ and $Fe^{3+}$ as well being present in soluble states (ionic and fine particulate), insoluble states (i.e., filterable), etc. Analysis and control of metal ions includes measurement or prediction of any combination (or all) of such permutations present in the system.

In different embodiments, changes in the filming inhibitor pump are limited in frequency. Preferably, adjustment limits are set at a maximum of 1 per 30 min and sequential adjustments in the same direction should not exceed 4. For example, after 4 total adjustments or a change of 50% or 100%, the pump could be suspended for an amount of time (e.g., 2 or 4 hours) and alarm could be triggered. If such a situation is encountered, it is advantageous to trigger an alarm to alert an operator. Other limits, such as maximum pump output may also be implemented. It should be appreciated that it is within the scope of the invention to cause any number of adjustments in any direction without limitation. Such limits are applied as determined by the operator.

Figure 5:
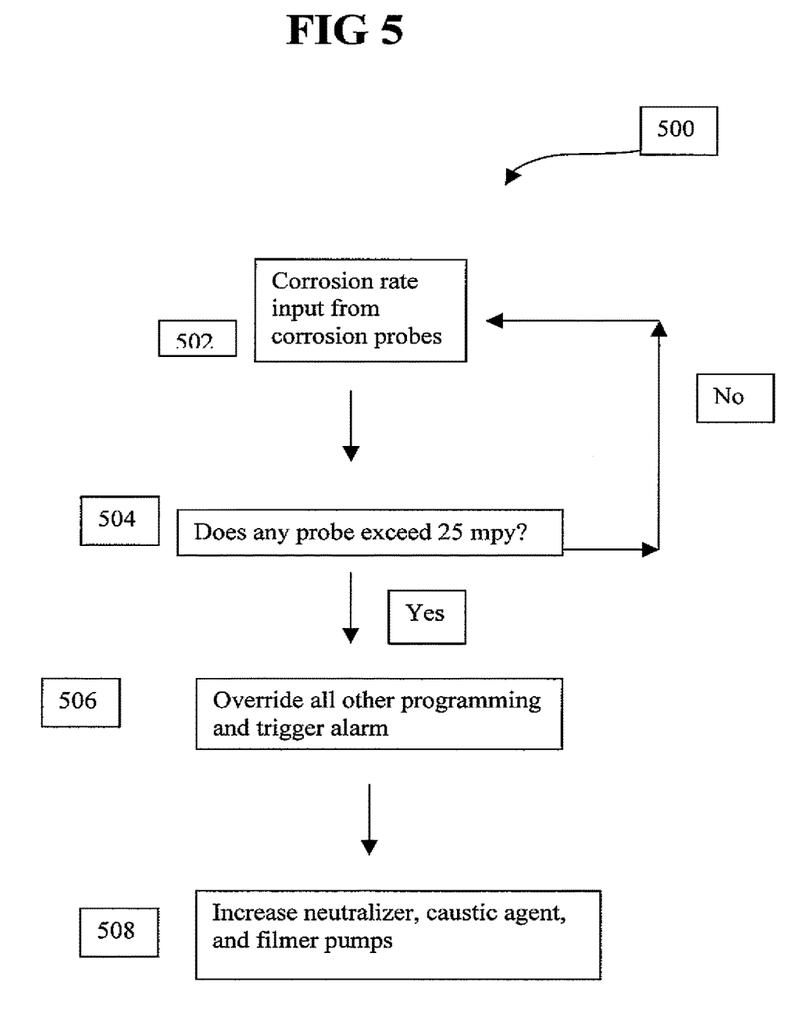
FIG. 5 depicts an embodiment of the invention for controlling the override of the introduction of neutralizer(s), caustic agent(s), and filming inhibitors into the system driven by the corrosion rates derived from one or more corrosion probes or other corrosion monitoring devices at any point in the system.

FIG. 5 depicts an embodiment of the invention as method 500 for controlling the override of the introduction of neutralizer(s), caustic agent(s), and filmers into the system driven by the corrosion rates derived from one or more corrosion probes or other corrosion rate sensing device at any point in the system. Most crude units use electrical resistance-type corrosion probes located at the inlet and/or the outlet of the overhead heat exchangers. Although any type of corrosion-sensing device is contemplated, the above-mentioned type is preferred.

Box 502 represents the one or more corrosion probes that provide information related to the corrosion rates in the system. The analyzer (e.g., controller or operator) determines whether the corrosion rate is greater than a predetermined rate (25 mpy in this example) as shown in box 504. The actionable corrosion rate is typically determined on a case-by-case basis by a skilled artisan and is dependent on a multitude of system factors. If the corrosion rate is less than a predetermined acceptable rate, the logic follows the "No" path and continues measuring and analyzing. If the corrosion rate is above the predetermined acceptable rate, the method includes overriding all other programming and triggering an alarm, as shown by box 506. In alternative embodiments, rather than an override other programming could be modified as determined by an operator or controller. In this example, the override includes increasing the neutralizer, caustic agent, and filmer pump rates by, for example 20%, as shown by box 508. In other embodiments, the pump rates are changed individually as determined by an operator or controller.

Although the corrosion probes (e.g., electrical resistance corrosion probes, linear polarization probes, and/or any other suitable method for determining metal loss) may be placed at any convenient location in the system, preferably they are placed in historically reliable locations in the system. In addition, if, for example, 2 overrides are activated over a 12 hr period, a reliability check is typically initiated to ensure that the corrosion probes are operating properly. If such a situation is encountered, it is advantageous to trigger an alarm to alert an operator. Other limits, such as maximum pump output may also be implemented. It should be appreciated that it is within the scope of the invention to cause any number of adjustments in any direction without limitation. Such limits are applied as determined by the operator.

The foregoing may be better understood by reference to the following examples, which are intended for illustrative purposes and are not intended to limit the scope of the invention.

Example 1

An exemplary embodiment of the invention would consist of a cluster of on-line analyzers in an explosion-proof box receiving a sample of water from a dew point water-sampling device. Data generated by these analyzers would be appropriately conditioned to send a control signal to various process chemical injection pumps. A Programmable Logic Controller (PLC) programmed by a skilled artisan would convert the raw data into pump control signals. A typical system would include one or more of the following components: chloride analyzer; iron analyzer; corrosion rate monitoring device; conductivity; pH meter; dew point water sample device; Class I, Div II explosion proof enclosure; PLC capable of multiple inputs/outputs; logic programming to convert chloride, pH, and iron data into pump speed control; and wireless or hard-wired connections from PLC to pumps.

Example 2

This instant invention would provide improvement in control for each of three test parameters of chloride ion concentration, pH, and iron ion concentration. Of these three, chloride is usually the most damaging if not properly controlled. The graph in FIG. 6 demonstrates how the invention would be capable of improving the control of chloride ion concentration (the dotted line indicates optimum concentration). A similar concept of better control through the method of the invention will apply to pH, iron ion concentration, and other system parameters ultimately resulting in corrosion rates reduced from previous levels and extending equipment run length.

Figure 6:
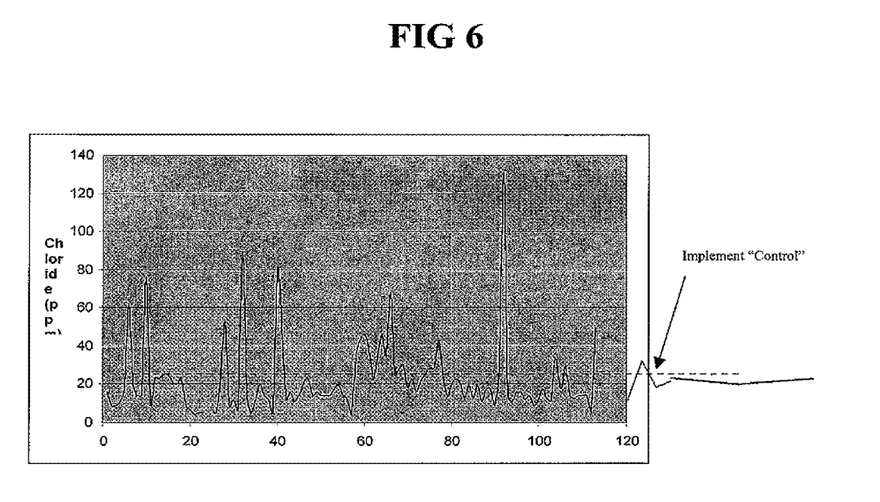
FIG. 6 shows a number of spikes of chloride concentration above the upper control limit from actual data from a crude unit and demonstrates how the method of the invention will be used to stabilize chloride ion concentration when tied to corrective action.

FIG. 6 shows a number of spikes of chloride concentration above the upper control limit from actual data from a crude unit. Chloride spikes are damaging to equipment and an ex post facto examination of the data will reveal increased corrosion and fouling during these episodes. Such spikes are more frequent and damaging when the crude slate is switched to a challenging or opportunity crude. Increased chloride ion concentration usually occurs with a concomitant increase in corrosion of the processing equipment and subsequent fouling due to deposition of corrosion byproducts. The section of the graph in FIG. 6 labeled "Implement Control" demonstrates how the method of the invention would be used to stabilize chloride ion concentration when more frequent data is available to minimize (or eliminate) disruptions.

Example 3

Figure 7:
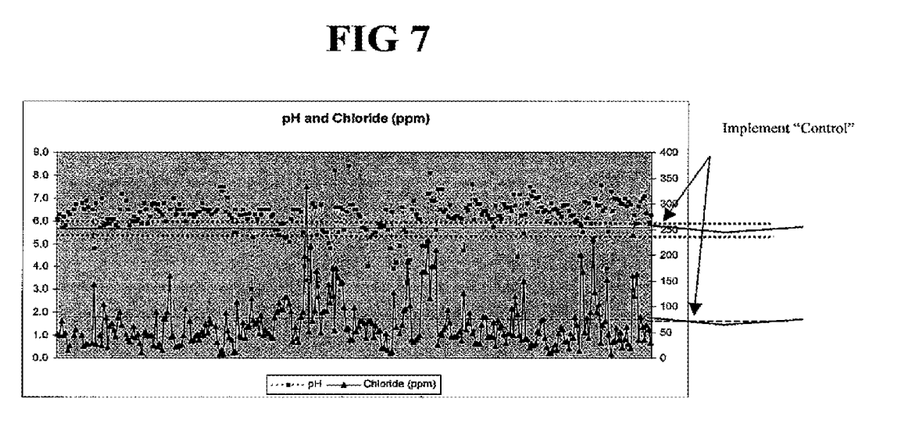
FIG. 7 shows pH and chloride ion concentration values tracked over time in an actual crude unit and demonstrates how the method of the invention will be used to stabilize these values.

The graph of FIG. 7 illustrates pH and chloride ion concentration values tracked over time for an actual crude unit (the dotted lines indicate optimum concentrations). It can be seen that a drop in the pH value usually accompanies upward spikes for chloride ion concentration. Such drops in pH typically result in increased corrosion and subsequent fouling (due to corrosion byproducts) of the heat exchanging equipment. The section of the graph labeled "Implement Control" demonstrates how the method of the invention would be used stabilize chloride ion concentration and pH, thus reducing corrosion and fouling in the system. Smoothing variation of the incoming chloride values allows for tighter pH control and more stable and predictable chemical usage.

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A method of optimizing a system parameter in a process stream of a crude unit, the method comprising:
   (a) introducing a challenging crude oil into a crude unit that previously contained a different kind of crude oil, the properties of the challenging crude differing such from the previous crude oil that it disrupts the steady state of the unit including causing a corrosion inducing spike in chloride concentration,
   (b) measuring and/or predicting a property associated with the system parameter at one or more points in the crude unit;
   (c) determining an optimum range associated with the measured and/or predicted property;
   (d) if the measured and/or predicted property is outside of the optimum range associated with that property, causing a change in an influx of a composition into the process stream, the composition capable of adjusting the property associated with the system parameter in a manner to bring the measured and/or predicted property within said optimum range; provided that adjustments are limited to no more than one per 30 minutes and if there are either four overall adjustments or the adjustment results in a change of at least 50% of added composition then further influx of composition is suspended for 4 hours; and
   (e) optionally repeating steps (b) to (d) for a plurality of different system parameters, each different system parameter having a unique associated property
   wherein the measuring/or predicting property comprises: collecting a sample of fluid from a process stream to form a sample stream; adding a sulfide scavenger obtained by reacting morpholine with formaldehyde to the sample stream; passing the sample stream through a membrane that prevents a reaction product of the sulfide scavenger and sulfide from flowing therethrough; and allowing the sample stream that flows through the membrane to contact a chloride specific electrode of a measurement cell to measure chloride content.

2. The method of claim 1, including: (i) converting the measured property into an input electrical signal capable of being transmitted to a controller and (ii) transmitting the input electrical signal to the controller.

3. The method of claim 2, including transmitting the input electrical signal via a wireless interface.

4. The method of claim 2, wherein the controller is operable to: (i) receive the transmitted input electrical signal; (ii) convert the received electrical signal into an input numerical value; (iii) analyze the input numerical value: (iv) generate an output numerical value; (v) convert the. output numerical value into an output electrical signal; and (vi) transmit the output electrical signal.

5. The method of claim 4, including transmitting the output electrical signal via a wireless interface.

6. The method of claim 4, wherein the controller is operable to: (i) analyze the input numerical value and (ii) determine if the input numerical value corresponds to the optimum range associated with the measured property.

7. The method of claim 6, wherein if the input numerical value does not correspond to the optimum range, the transmitted output electrical signal causing the change in the influx of the composition into the process stream, the composition capable of adjusting the property associated with the system parameter in a manner to cause the input numerical value to correspond to the optimum input range.

8. The method of claim 1, including continuously or intermittently measuring and/or predicting the system parameter.

9. The method of claim 1, including monitoring the system parameter in real time.

10. The method of claim 1, including a plurality of different compositions, wherein an influx of one or more of the different compositions into the process stream are collectively and/or individually capable of adjusting the property associated with the system parameter.

11. The method of claim 1, wherein the plurality of different system parameters is selected from the group consisting of: pH, chloride ion concentration; iron ion concentration; non-iron Metal ion concentration; corrosion rate; and combinations thereof.

12. The method of claim 11, wherein the crude unit has a plurality of components including an atmospheric tower with at least one heat exchanger, and wherein the pH and chloride ion concentration are derived from a dew point water sample and/or an accumulator boot water sample in the crude unit and the iron ion concentration or the non-iron metal ion concentration is derived from the accumulator hoot water sample in the crude unit.

13. The method of claim 12, including obtaining the dew point water sample and/or the boot water sample with an online, optionally automated, sampling device.

14. The method of claim 1, wherein the optimum range is user-defined.

15. The method of claim 1, including operating the method continuously, automatically, and online or on a batch basis.

16. The method of claim 1, including operating the method either simultaneously or sequentially for at least two of the different system parameters.

17. The method of claim 1, including operating the method over a network.

18. The method of claim 1, further comprising selecting the system parameter to reduce corrosion and/or corrosion byproduct deposition in the crude unit.

19. The method of claim 1, further comprising selecting the system parameter to optimize preheating operations to keep product and/or effluent water within specifications.

20. The method of claim 1, further comprising selecting the system parameter to optimize desalting operations to keep product and/or effluent water within specifications.

21. The method of claim 1, farther comprising selecting the system parameter to optimize distilling operations to keep product and/or effluent water within specifications.

* * * * *

UNITED STATES PATENT AND TRADEMARK OFFICE
CERTIFICATE OF CORRECTION

PATENT NO. : 9,611,431 B2  
APPLICATION NO. : 14/874675  
DATED : April 4, 2017  
INVENTOR(S) : Glenn L. Scattergood et al.

Page 1 of 1

It is certified that error appears in the above-identified patent and that said Letters Patent is hereby corrected as shown below:

In the Claims

At Column 12, Line 42, change "convert the. output" to --convert the output--

Signed and Sealed this  
Sixth Day of June, 2017

Michelle K. Lee  
*Director of the United States Patent and Trademark Office*